United States Patent [19]

Arndt et al.

[11] Patent Number: 5,559,257
[45] Date of Patent: Sep. 24, 1996

[54] PROCESS FOR THE PREPARATION OF TETRACHLORO-1,4-BENZOQUINONE

[75] Inventors: Otto Arndt, Hofheim; Wolfgang Tronich, Eppstein, both of Germany

[73] Assignee: Hoechst A G, Germany

[21] Appl. No.: 392,469

[22] Filed: Feb. 22, 1995

[30] Foreign Application Priority Data

Feb. 24, 1994 [DE] Germany .......................... 44 05 929.9

[51] Int. Cl.⁶ .................................................. C07C 50/20
[52] U.S. Cl. .................................................. 552/308
[58] Field of Search ............................................. 552/308

[56] References Cited

U.S. PATENT DOCUMENTS

| | | | |
|---|---|---|---|
| 5,075,462 | 12/1991 | Kuo et al. ................................ | 552/299 |
| 5,075,463 | 12/1991 | Kuo et al. ................................ | 552/299 |
| 5,149,850 | 9/1992 | Arndt et al. . | |
| 5,151,532 | 9/1992 | Arndt et al. ............................. | 552/308 |

FOREIGN PATENT DOCUMENTS

| | | |
|---|---|---|
| 0220135 | 11/1991 | European Pat. Off. . |
| 0278378 | 1/1992 | European Pat. Off. . |
| 5-155804 | 6/1993 | Japan . |

OTHER PUBLICATIONS

Ullmann's Encyclopedia of Industrial Chemistry, 5th Ed., vol A8, pp. 342–348 (1987).
European Search Report No. 95101915.7, dated Jun. 13, 1995.

*Primary Examiner*—Kimberly J. Prior
*Attorney, Agent, or Firm*—Connolly & Hutz

[57] ABSTRACT

The invention relates to a process for the preparation of tetrachloro-1,4-benzoquinone of high purity by the action of chlorine and concentrated hydrochloric acid on hydroquinone, which involves introducing a portion of the hydroquinone to be employed into initially introduced hydrochloric acid containing catalytic amounts of iron(III) ions and an anionic dispersant, introducing chlorine gas into this solution at a temperature from 20° to 107° C., then adding the residual quantity of hydroquinone as a solid or in solution, raising the temperature to from 80° to 107° C. while continuing to pass in gaseous chlorine, adding, after the introduction of gaseous chlorine has ended, a relatively high-boiling organic solvent which is not miscible with hydrochloric acid, and subsequently subjecting the reaction mixture to thermal aftertreatment.

19 Claims, No Drawings

PROCESS FOR THE PREPARATION OF TETRACHLORO-1,4-BENZOQUINONE

The invention relates to a process for the preparation of tetrachloro-1,4-benzoquinone of high purity and improved physical properties by chlorination of hydroquinone using chlorine in aqueous hydrochloric acid and aftertreatment of the chlorination suspension with an organic solvent.

Tetrachloro-1,4-benzoquinone (chloranil) is a useful intermediate for the preparation of dyes. It is also employed as a photographic chemical and vulcanizing agent and used as an additive for lubricants.

The preparation of chloranil from hydroquinone (1,4-dihydroxybenzene) or 1,4-benzoquinone or chlorinated 1,4-benzoquinone is known.

Patent EP 0 220 135 describes, for example, a process in which hydrochloric acid and chlorine are initially introduced under pressure and chlorine and quinone, hydroquinone or their chlorinated derivatives are metered in under pressure in separate streams.

Patent EP 0 278 378 describes a process in which the total quantity of hydroquinone is initially introduced with hydrochloric acid, and chlorine is then introduced as a gas at atmospheric pressure according to a specific temperature and dilution program.

Japanese Patent Application JP 05155804 describes a process in which hydroquinone, for example, is treated with chlorine gas in a mixture of 25% strength hydrochloric acid and a solvent which is not miscible with aqueous hydrochloric acid but is resistant to chlorine (e.g. o-dichlorobenzene), for 7 hours at a hydrogen chloride pressure of about 2 bar at 80° C. The suspension is cooled to room temperature, filtered, and the chloranil on the filter is washed with water and finally with methanol.

These procedures have disadvantages:

The process according to EP 0 220 135 uses a chlorine pressure of from 3 to 12 bar and requires a precise, synchronized addition of the chlorine and hydroquinone streams.

The process according to EP 0 278 378 has the following disadvantages:

1.) As a result of the initial introduction of the total quantity of hydroquinone, crusts are formed on the reactor wall in the course of the reaction. In addition, the reaction mixture goes through states of poor stirrability, as it becomes very thick during this process.

2.) The prolonged thermal loading of the reaction mixture at temperatures above 100° C. causes an impairment of quality owing to traces of by-products.

3.) The long after-chlorination period brings about a worsening of the space-time yield.

The process according to JP 05155804 is restricted to solvents which do not react with chlorine, and also the solvent is added in a volume ratio of 1:0.1–10, preferably 1:0.5–5. This reduces the reactor capacity and therefore also reduces the space-time yield. The polychlorinated and toxicologically objectionable secondary components (pentachlorophenol etc.) which are dissolved in the solvents mentioned in the description are difficult to dispose of by chemical means (for example by cleaving the C—Cl bond on reaction with sodium glycolares). Chlorinated organic solvents which remain in the distillation residue consume additional cleaving agent and lead to problems because of the agglomeration of the cleavage mixture. The Japanese application also mentions nitrobenzene which, at the high temperatures of around 200° C. which are required for the cleavage, brings about an increase in risk owing to a rise in the potential for thermal decomposition.

The disposal of the organic solvents which are obtained in this process requires special technical measures because of the dioxin problem.

There is therefore a demand for a process for the preparation of tetrachloro-1,4-benzoquinone which is simple and technically easy to carry out, avoids the abovementioned disadvantages and makes tetrachloro-1,4-benzoquinone accessible not only in high purity, high yield and space-time yield and high bulk density but also enables the simple and cost-effective disposal of the toxicologically objectionable, chlorine-containing by-products.

This object is achieved by a process for the preparation of tetrachloro-1,4-benzoquinone of high purity by the action of chlorine and concentrated hydrochloric acid on hydroquinone, which comprises introducing a portion of the hydroquinone to be employed into initially introduced hydrochloric acid containing catalytic amounts of iron(III) ions and an anionic dispersant, introducing chlorine gas into this solution at a temperature from 20° to 107 ° C., then adding the residual quantity of hydroquinone as a solid or in solution, raising the temperature to from 80° to 107° C. while continuing to pass in gaseous chlorine, adding, after the introduction of gaseous chlorine has ended, a relatively high-boiling organic solvent which is not miscible with hydrochloric acid, and subsequently subjecting the reaction mixture to thermal aftertreatment.

The organic solvent is advantageously added in a quantity of from 0.05 to 2 parts per part of tetrachloro-1,4-benzoquinone.

A procedure has proven suitable which comprises introducing a portion of the hydroquinone to be employed into an initially introduced 4- to 6-fold molar quantity—based on the total quantity of hydroquinone—of from 20% to 37% strength aqueous hydrochloric acid containing catalytic amounts of iron(III) ions and an anionic dispersant, introducing from 1.5 to 2.0 times the molar quantity based on total hydroquinone—of chlorine gas into this solution at a temperature of from 20° to 90° C., then adding the remaining quantity of hydroquinone as a solid or in solution, introducing from 1.5 to 2.0 times the molar quantity of chlorine gas, while keeping the concentration of the hydrochloric acid initially at from 25% to 31% by addition of water, raising the temperature to from 100° to 107° C. while continuing to pass in gaseous chlorine (from 1.3 to 1.9 times the molar quantity) and while diluting with water to a hydrochloric acid concentration of from 20% to 22%, adding, when the introduction of gaseous chlorine has come to an end, a relatively high-boiling organic solvent which is not miscible with hydrochloric acid, in a quantity of from 0.15 to 1.0 part per part of tetrachloro-1,4-benzoquinone or in a quantity of about 2%–10% by weight, based on the reaction mixture, and then subjecting the reaction mixture to thermal aftertreatment.

In many cases it has proven suitable to employ from 22% to 33% strength, in particular 31% strength, hydrochloric acid or mother liquor (recycled acid) containing from about 20% to 22% of HCl and to carry out the first phase of the chlorination at a temperature of from 40° to 90° C., in particular from 50° to 80° C. It has proven advantageous to introduce initially from 30% to 70%, in particular from 40% to 60% and preferably from 45% to 55%, of the hydroquinone to be employed and to adjust the concentration of the hydrochloric acid to from 22% to 28%, in particular from 23% to 25%.

The duration of the chlorination is advantageously from 5 to 15 hours, in particular from 8.5 to 10.5 hours.

It has proven favorable to add the organic solvent which is not miscible with hydrochloric acid in a quantity of from 0.2 to 0.5 part per part of tetrachlorobenzoquinone or in a quantity of from 2% to 4% by weight based on the reaction mixture.

Solvents which have proven suitable are aromatic hydrocarbons, in particular xylene, toluene or diisopropylnaphthalene; in principle, of course, halogenated aromatic compounds such as, for example, chlorobenzene can also be employed, but these have no advantages for the reasons given above.

The thermal aftertreatment is advantageously carried out at from 90° to 100° C. under atmospheric pressure.

Surprisingly, substantial improvements in space-time yield and product quality are achieved by this procedure in comparison to EP 0 278 378. The process modification is that the total quantity of hydroquinone is no longer introduced initially, but instead the hydroquinone is added to the mixture in two portions: the first portion as an initial charge together with the hydrochloric acid, and the second portion as a solid or in aqueous solution at a strength of from about 10% to 20%, in particular from 15% to 18%, as a single addition at elevated temperature after the first introduction of gaseous chlorine. While this is done water is flowing in in a constant stream, so that the concentration of the hydrochloric acid is maintained at from about 25% to 31%. After completion of the first chlorination stage the introduction of gaseous chlorine is continued, but now with an increase in temperature to close to the boiling point of the azeotropic hydrochloric acid (from about 105° to 107° C.), whose concentration of about 20% to about 22% is regulated by addition of water.

The process modification compared with JP 5 155 804 is that the organic solvent is not added until after the chlorination and in any case is added in a substantially smaller quantity—a "catalytic amount", so to speak (e.g. about 2%–4% by weight based on the reaction mixture).

The advantages of this procedure over EP 0 278 378 are that the ease of industrial implementation of the reaction is improved: the stirrability is made easier despite decreased use of hydrochloric acid, the heat transfer is improved, the cooling brine is unnecessary, the homogeneity of the reaction mixture is produced by the absence of crusts, the time consumption on chlorination and oxidation is reduced, the quantity of chlorine gas and therefore also the waste gas pollution by chlorine is decreased, and the quality of the product (evident from fewer components in the HPLC) and its reproducibility are improved.

The advantages of this procedure over that of Japanese application JP 05155804 are that the organic solvent is only added in very low quantities: a "catalytic amount", so to speak. This produces a better utilization of reactor capacity. The organic solvent need not be resistant to chlorine, widening the range of available solvents. The widening in the solvent range enables "tailor-made" process conditions for the disposal of the polychlorinated secondary components by incineration or chemical cleavage.

The moist chloranil filter product which is isolated from the reaction mixture by filtration following the aftertreatment ("finishing") with organic solvent contains water and "finishing agent". Both of these components are washed out with, for example, an alcohol, preferably methanol or ethanol. The alcohol can be recovered from the washing filtrate by fractional distillation. The distillation residue contains the polychlorinated secondary components in enriched form, and it proves advantageous for the bottom product in the distillation to remain stirrable because of the presence of organic solvent, so that it can easily be removed from the vessel. In this form the polychlorinated secondary components are passed on for disposal.

The treatment of this residue with the sodium salt of ethylene glycol and/or butylpolyglycol in a mixture with glycol/tetraethylene glycol dimethyl ether/optionally diisopropylnaphthalene at temperatures of from 185° to 195° C. gave cleaving results, after 7 hours, of up to about 97% cleavage of the C—Cl bond to produce chloride.

If a chlorine-containing organic solvent were used, a portion thereof would likewise accumulate in the bottom product in the distillation and would lead to an increased consumption of cleavage agent (glycolate).

The process is flexible in terms of temperature control and in the manner of addition of the second portion of hydroquinone.

The reasons for the improved process control and improved reproducibility in comparison with the cited prior art are a) working at atmospheric pressure (safety aspects), b) simpler conditions of metered addition (a temporary over-addition of chlorine is harmless with respect to waste-gas pollution, since the chlorine is buffered by the excess hydroquinone present). The 2nd portion of hydroquinone can be added rapidly as a solid or as an aqueous solution before further gaseous chlorine is introduced, or slowly simultaneously with the further introduction of gaseous chlorine, c) the simpler cooling technique (cooling at a higher temperature level), d) the improved stirrability of the suspension despite a decreased initial hydrochloric acid charge, e) the lower tendency toward crust formation, f) the decrease in chlorine in the waste gas, g) the absence of hydrogen chloride from the waste gas, h) the more rapid oxidation of the polychlorinated quinhydrones and hydroquinones, which are formed as intermediates, by the chlorine, i) the lower thermal loading during the afterchlorination, j) the freedom from dependence on the composition of the gas atmosphere in the reactor (air or nitrogen), k) the consistent quality of the isolated chloranil, which means that recrystallization is unnecessary, and l) the production of the chloranil in the form of larger crystals and therefore in higher bulk density. The electrostatic charging has also disappeared.

The chloranil prepared in accordance with the invention is of high purity (melting point, HPLC) and, in comparison with the indications in the cited EP 0 278 378, contains fewer secondary components while at the same time exhibiting an increased space-time yield.

Moreover, the aftertreatment with the organic solvent (here termed "finishing") brings about a considerable increase in the average particle size (from about 10–20 μm to about 50–100 μm) whereas the factor for the breadth of the particle size distribution undergoes a marked decrease (from about 2.3 to 1.3). The difference is clearly evident to the eye under the optical microscope or scanning electron microscope. There is thus an accompanying fall in the "tamping volume" of the crystalline powder (or a rise in the bulk density and vibration density). In addition, the electrostatic charging which is observed without aftertreatment (finishing) has disappeared because of the reduction in the overall surface area. Flowability is improved and the dust explosion tendency is reduced.

The examples which follow serve to illustrate the process according to the invention without limiting it. In these examples parts are by weight.

EXAMPLE 1

First stage 27.7 Parts of hydroquinone (0.25 mol) are introduced as a solid into 287 parts of 31% hydrochloric acid (2.4 mol) which contains 0.12 part or iron(III) chloride as oxidation catalyst and 0.50 part of an anionic dispersant. 125 Parts of chlorine (1.76 mol) are introduced as a gas at 70° C. over 3 hours. 250 Parts of hot water (70° C.) are run in simultaneously. When 50% of the chlorine and of the water has been added, an additional 27.7 parts of hydroquinone (0.25 mol) in solid form are added in a single portion.

This second portion of hydroquinone may also be metered in in the form of a solution in 125 parts of hot water (70° C.), the rate of metered addition (preferably 10 minutes, max. 1.5 hours) not being critical. In this case the quantity of solution water is adjusted with respect to the quantity of water run in so that only 125 parts of water are run in instead of the abovementioned 250 parts. A readily stirrable, crust-free, brownish yellow suspension is obtained. The waste gas is monitored. No chlorine nor hydrogen-chloride may pass into the waste gas. The concentration of the hydrochloric acid is about 25%.

Second stage

The reaction mixture is heated to 90° C. over 3 hours with further introduction of 45 parts of gaseous chlorine (=0.63 mol). The concentration of the hydrochloric acid is about 28%. A readily stirrable, crust-free, pale yellow suspension is formed.

The waste gas is monitored. Still no chlorine may escape or pass into the waste gas.

Dilution with water

200 Parts of water are run in over 15 minutes. The HCl concentration subsequently is about 21%.

Third stage

The thin, pale yellow suspension is heated to 105° C. over 2 hours while passing in 12.5 parts of gaseous chlorine (=0.18 mol).

At this stage the reaction mixture contains less than 10 mol % of trichlorobenzoquinone, according to TLC analysis.

Fourth stage

The temperature of the reaction mixture is held at 103°–106° C. preferably 105° C. for 1.5 hours during this time further gaseous chlorine is introduced in a maximum quantity of 10 parts =0.14 mol. The reaction mixture contains less than 5 mol % of trichlorobenzoquinone.

All of the stages are carried out in an open system (ventilation via a waste-gas unit) so that no pressure build up can occur.

The overall chlorination time is max. 10 hours, with a total of 192.5 parts of gaseous chlorine (2.71 mol) being introduced during this period.

Treatment with xylene

25 Parts of xylene are run into the product suspension, whose temperature is 100° C. After a few minutes the suspension becomes distinctly less viscous. Product suspension which adheres to the vessel wall by splashing is quickly washed back down by refluxing xylene. Stirring is continued at 100° C. for 1–2 hours. The reaction mixture now contains less than 1 mol % of trichlorobenzoquinone.

The treatment with xylene on the one hand improves the quality of the chloranil and on the other hand results in a substantial increase in crystal size.

Isolation of the chloranil

The mixture is cooled to 30° C. while blanketing with protective gas (nitrogen) to prevent sucking-back of chlorine from the waste-gas absorption and for detoxifying the atmosphere over the reaction mixture. After filtration at 30° C. and washing with 200 parts of methanol first of all and then with 500 parts of hot water, 115 parts of chloranil are obtained with a purity of 99.0% (=0.463 mol), corresponding to a yield of 92.6% of theory. Impurities such as tetrachlorohydroquinone and polychlorinated quinhydrones and hydroquinones are not detectable (TLC). The content of 2,3,5-trichlorobenzoquinone is not more than 1.0 mol % (HPLC). The content of pentachlorophenol is from 0 to not more than 10 μg/g (HPLC). The particle size distribution (Malvern, laser light diffraction, without ultrasound treatment) shows a maximum at 100 μm. The product is readily flowable. The mother liquor is hydrochloric acid with a concentration of about 21%. The methanolic washing filtrate contains almost the total quantity of xylene. The methanol is regenerated from the methanolic washing filtrate by distillation. The bottom product from distillation can be disposed of by incineration. It contains pentachlorophenol and other secondary components containing organically bonded chlorine. These may of course also be disposed of by chemical means, for example by treatment with glycolates, in which case the presence of xylene, which does not itself contain chlorine, is not a hindrance.

The mother liquor containing 21% of HCl can be recycled after the removal of very small quantities of xylene, for example by means of activated charcoal, or can be disposed of in the usual way.

The chlorine balance (hydrogen chloride+chlorine, incl. waste gas) is about 95% of theory.

The chlorine conversion is about 99%–100% of theory.

EXAMPLE 2

The procedure is as in Example 1, but using the mother liquor as the initial charge of recycled acid. Instead of the 287 parts of 31% strength hydrochloric acid mentioned in Example 1, 415 parts of the mother liquor from Example 1 which has been clarified over activated charcoal (=50% of the total quantity of mother liquor obtained) containing 87.5 parts of HCl are used. Since this mother liquor now contains from 125 to 130 parts of additional water, only the second half (from 1.5 hours) of the 250 parts of water mentioned in the first stage of Example 1 are run in at 70° C., or, if—as described in Example 1—the second portion of hydroquinone is employed as a solution in 125 parts of water, no further water is now metered in in the first stage.

After filtration at 30° C. and washing with 200 parts of methanol first of all and then with 500 parts of hot water, 110 parts of chloranil are obtained having a purity of at least 99.0% (=0.443 mol), corresponding to a yield of 88.6% of theory. Impurities such as tetrachlorohydroquinone and polychlorinated quinhydrones and hydroquinones are no longer detectable (TLC). The content of 2,3,5-trichlorobenzoquinone is not more than 1.0 mol % (HPLC). The content of pentachlorophenol is from 0 to not more than 10 μg/g (HPLC). The particle size distribution (Malvern, laser light diffraction, without ultrasound treatment) shows a maximum at 100 μm. The product is readily flowable.

The mother liquor is hydrochloric acid with a concentration of about 21%. The methanolic washing filtrate contains almost the entire quantity of xylene. The methanol is regenerated from the methanolic washing filtrate by distillation; a content of xylene is not a hindrance. The bottom product from distillation can be disposed of by incineration. It contains pentachlorophenol and other secondary components containing organically bonded chlorine. These may of course also be disposed of by chemical means, for example by treatment with glycolates, in which case the presence of xylene, which does not itself contain chlorine, is not a hindrance. The mother liquor containing 21% of HCl can be partially recycled after clarification to remove very small quantities of xylene by, for example, activated charcoal, or can be disposed of in the usual way. The chlorine balance (hydrogen chloride+chlorine, incl. waste gases) is about 95% of theory.

The chlorine conversion is about 99%–100% of theory.

EXAMPLE 3

The procedure is as in Example 1 but using 40 g of xylene for finishing the crystals and ethanol for washing the chloranil on the suction filter. The product suspension is filtered at 30° C. The filter product is washed at 25° C. with 200 parts of ethanol. Ethanol-moist chloranil and an ethanolic washing filtrate (which contains the major proportion of the xylene) are obtained. After washing with hot water and drying, 115 parts of chloranil are obtained with a purity of at least 99.0% (=0.463 mol), corresponding to a yield of 92.6% of theory. Impurities such as tetrachlorohydroquinone and polychlorinated quinhydrones and hydroquinones are not detectable (TLC). The content of 2,3,5-trichlorobenzoquinone is not more than 1.0 mol % (HPLC). The content of pentachlorophenol is <5 µg/g (HPLC).

The particle size distribution (Malvern, laser light diffraction, without ultrasound treatment) shows a maximum at 99 µm. The product is readily flowable. The mother liquor is hydrochloric acid with a concentration of from about 21% to 22%. It can be partially recycled after removal of a small quantity of xylene, for example by activated charcoal, or can be disposed of in the usual way. The ethanol is regenerated from the ethanolic washing filtrate by distillation. The bottom product from distillation can be disposed of by incineration. It contains pentachlorophenol and other secondary components containing organically bonded chlorine. These may of course also be disposed of by chemical means, for example by treatment with glycolares, in which case the presence of xylene, which does not itself contain chlorine, is not a hindrance.

The chlorine balance (hydrogen chloride+chlorine, incl. waste gas) is about 95% of theory.

The chlorine conversion is about 99%–100% of theory.

EXAMPLE 4

The procedure is as in Example 1 but using xylene both for finishing the crystals and for washing the chloranil on the suction filter. The product suspension is filtered at 30° C. The filter product is washed at 25° C. with 100 parts of xylene.

Xylene-moist chloranil (which contains xylene from finishing) and a xylenic washing filtrate are obtained. After washing with hot water and drying, 111.6 parts of chloranil are obtained with a purity of 99.5% (=0.452 mol), corresponding to a yield of 90.3% of theory.

Impurities such as tetrachlorohydroquinone and polychlorinated .quinhydrones and hydroquinones are not detectable (TLC). The content of 2,3,5-trichlorobenzoquinone is 0.3 mol % (HPLC).

The content of pentachlorophenol is less than 5 µg/g (HPLC).

The particle size distribution (Malvern, laser light diffraction, without ultrasound treatment) shows a maximum at 100 µm. The product is readily flowable. The mother liquor is hydrochloric acid with a concentration of about 22%. It can be partially recycled after clarification to remove traces of xylene, for example using activated charcoal, or can be disposed of in the usual way.

The xylene is regenerated from the xylenic washing filtrate by distillation. The bottom product from distillation can be disposed of by incineration. It contains pentachlorophenol and other secondary components containing organically bonded chlorine. These may of course also be disposed of by chemical means, for example by treatment with glycolates, in which case the presence of xylene, which does not itself contain chlorine, is not a hindrance.

The chlorine balance (hydrogen chloride+chlorine, incl. waste gas) is about 98% of theory. The chlorine conversion is about 99%–100% of theory.

EXAMPLE 5

The procedure is as in Example 1 but using chlorobenzene both for finishing the crystals and for washing the chloranil on the suction filter. After addition of only 20 parts of chlorobenzene at 100° C. the suspension becomes clearly less viscous. Product suspension which adheres to the reactor wall is washed back into the reaction mixture. The finishing of the crystals is carried out with 40 parts of chlorobenzene (to about 1100 parts of reaction mixture) at 100° C. within 2 hours. The chloranil is filtered from the reaction mixture at 90° C.

The chlorobenzene (from crystal finishing) remains quantitatively in the filter product. The filter product is washed at 25° C. with 200 parts of chlorobenzene. About 150 to 155 parts of chlorobenzene-moist chloranil and a chlorobenzenic washing filtrate, which goes for regeneration of chlorobenzene and disposal of the polychlorinated secondary components present therein, are obtained. The residual chlorobenzene is stripped off from the chlorobenzene-moist chloranil using steam (=about 10 to 20 parts). The aqueous suspension which is free of chlorobenzene is filtered at 90° C. and washed with 500 parts of hot water.

112 Parts of chloranil are obtained with a purity of at least 99.0% (=0.451 mol), corresponding to a yield of 90.2% of theory.

Impurities such as tetrachlorohydroquinone and polychlorinatedquinhydrones and hydroquinones are not detectable (TLC). The content of 2,3,5-trichlorobenzoquinone is from 0.3 to not more than 1.0 mol % (HPLC). The content of pentachlorophenol is from 0 to not more than 5 µg/g (HPLC).

The particle size distribution (Malvern, laser light diffraction, without ultrasound treatment) shows a maximum at 51 µm. The product is readily flowable. The mother liquor is hydrochloric acid with a concentration of about 20% to 21%. It can be partially recycled after clarification to remove very small quantities of chlorobenzene by, for example, activated charcoal, or can be disposed of in the usual way. The chlorobenzene is regenerated from the chlorobenzenic washing filtrate by distillation. The bottom product from distillation contains pentachlorophenol and other secondary components containing organically bonded chlorine. These can of course be disposed of by chemical means, for example by treatment with glycolates, in which case, however, residual chlorobenzene must first of all be removed by steam distillation.

The chlorine balance (hydrogen chloride+chlorine, incl. waste gas) is about 95% of theory.

The chlorine conversion is about 99%–100% of theory.

EXAMPLE 6

The procedure is as in Example 1 but this time using toluene instead of xylene as "finishing agent" and using toluene and ethanol instead of methanol to wash the chloranil on the suction filter.

After filtration at 30° C. and washing with 50 parts of toluene first of all and then with 200 parts of methanol and finally with 500 parts of hot water, 113 parts of chloranil are obtained with a purity of at least 99.0% (=0.455 mol), corresponding to a yield of 91.0% of theory. Impurities such as tetrachlorohydroquinone and polychlorinated quinhydrones and hydroquinones are not detectable (TLC). The content of 2,3,5-trichlorobenzoquinone is 0.4 mol % (HPLC).

The content of pentachlorophenol is from 0 to not more than 10 μg/g (HPLC).

The particle size distribution (Malvern, laser light diffraction, without ultrasound treatment) shows a maximum at 100 μm. The product is readily flowable.

The mother liquor is hydrochloric acid with a concentration of about 22%. The ethanolic washing filtrate contains almost the entire quantity of toluene. The ethanol is regenerated from the ethanolic washing filtrate by distillation. In this case a content of toluene is not a hindrance. The bottom product from distillation can be disposed of by incineration. It contains pentachlorophenol and other secondary components containing organically bonded chlorine. These can of course also be disposed of by chemical means, for example by treatment with glycolates, in which case the presence of toluene, which does not itself contain chlorine, is not a hindrance. The mother liquor containing 22% of HCl can be partially recycled after clarification to remove very small quantities of toluene, for example by means of activated charcoal, or can be disposed of in the usual way.

The chlorine balance (hydrogen chloride+chlorine, incl. waste gas) is about 95% of theory.

The chlorine conversion is about 99% to 100% of theory.

EXAMPLE 7

Comparative Example (procedure without employing organic solvent)

The procedure is as in Example 1, but using no organic solvent either for finishing the crystals or for washing the chloranil on the suction filter.

119 Parts of chloranil are obtained with a purity of 97.0% (=0.469 mol) corresponding to a yield of 93.9% of theory.

Impurities such as tetrachlorohydroquinone and polychlorinated quinhydrones and hydroquinones are not detectable (TLC). The content of 2,3,5-trichlorobenzoquinone is from 2.5 to 3.0 mol % (HPLC). The content of pentachlorophenol is 220 μg/g (HPLC).

The particle size distribution (Malvern, laser light diffraction, without ultrasound treatment) shows a maximum at 12 μm. The product has a poor flowability and is electrostatically charged.

The mother liquor is hydrochloric acid with a concentration of about 20% to 21%. The chlorine balance (hydrogen chloride+chlorine, incl. waste gas) is about 97% of theory. The chlorine conversion is about 99%–100% of theory.

EXAMPLE 8

Comparative Example from Ciba Patent see EP 0 220 135, Example 2

EXAMPLE 9

(Comparative example from Japanese disclosure 5 155 804, Implementation Example 1)

A glass autoclave is charged with 400 ml of o-dichlorobenzene, 400 ml of 25% strength hydrochloric acid and 81.6 g of hydroquinone (0.74 mol). The mixture is heated to 80° C. Then 288.6 g of gaseous chlorine are passed in over 7 hours. Stirring is continued for 1 hour. As the reaction progresses the pressure in the autoclave increases. As soon as a pressure of 2 kg/cm$^2$ has been reached (after 2 mol of chlorine, based on 1 mol of hydroquinone), this pressure is maintained at a constant level until the end of the reaction by means of a limiting control valve in the waste-gas line. After it has been cooled to room temperature, the crystalline product is filtered off via a glass suction filter and the crystals are washed with three times 200 ml of water and with three times 200 ml of methanol.

178.5 g of chloranil are obtained (yield=98.1%). The purity according to GC analysis is 99.85% (trichlorobenzoquinone =0.15%).

We claim:

1. A process for the preparation of tetrachloro-1,4-benzoquinone of high purity in a reactor by the action of chlorine and concentrated hydrochloric acid on hydroquinone, which comprises the steps of:
   a) introducing hydrochloric acid containing catalytic amounts of iron (III) ions and an anionic dispersant into the reactor;
   b) introducing a portion of the hydroquinone to be employed into the reactor containing the hydrochloric acid to form a solution,
   c) introducing chlorine gas into the solution at a temperature from 20° to 107° C.,
   d) adding the residual quantity of hydroquinone as a solid or in solution,
   e) raising the temperature to from 80° to 107° C. while continuing to pass in gaseous chlorine,
   f) adding, after the introduction of gaseous chlorine has ended, a relative high-boiling organic solvent which is not miscible with hydrochloric acid, and
   g) subsequently subjecting the reaction mixture to thermal aftertreatment.

2. The process as claimed in claim 1, wherein the organic solvent is added in a quantity of from 0.05 to 2 parts per part of tetrachloro-1,4-benzoquinone.

3. The process as claimed in claim 1, wherein from 30% to 70% of the hydroquinone to be employed is introduced in step b).

4. The process as claimed in claim 1, wherein a from 22 to 33% strength introduced in step a).

5. The process as claimed in claim 1, wherein recycled hydrochloric acid in the form of a mother liquor whose concentration is about 20%–22% is employed.

6. The process as claimed in claim 1, wherein the gaseous chlorine is introduced at a temperature of from 40° to 90° C. in step c).

7. The process as claimed in claim 1, wherein the residual quantity of the hydroquinone is added in the form of a from 10% to 20% strength aqueous solution.

8. The process as claimed in claim 1, wherein the chlorination is carried out over from 5 to 15 hours.

9. The process as claimed in claim 1, wherein after the introduction of gaseous chlorine has ended, the organic solvent which is not miscible with hydrochloric acid added in step f) is added in a quantity of from 0.2 to 0.5 part per part of tetrachlorobenzoquinone, or in a quantity of from 2% to 4% by weight based on the reaction mixture.

10. The process as claimed in claim 1, wherein the solvent employed is an aromatic hydrocarbon.

11. The process as claimed in claim 1 wherein the thermal aftertreatment is carried out at from 90° to 100° C. under atmospheric pressure.

12. The process as claimed in claim 1, wherein the hydrochloric acid introduced in step a) is introduced in a 4 to 6 fold molar quantity, based on the total quantity of hydroquinone, and is introduced at of from 20% to 30% strength;

the chlorine gas introduced in step c) is introduced at a temperature of from 20° to 90° C. and in an amount of from 1.5 to 2.0 times the molar quantity of hydroquinone;

the passing in of the gaseous chlorine in step e) is carried out by e1) introducing chlorine gas in an amount of from 1.5 to 2.0 times the molar quantity of hydroquinone, while maintaining the concentration of hydrochloric acid at from 25% to 31% by the addition of water;

e2) raising the temperature to from 100° to 107° C. while passing chlorine as in an additional 1.3 to 1.9 molar amount, and diluting the solution with water to a hydrochloric acid concentration of from 20% to 22%;

the solvent added in step f) is added in a quantity of from 0.15 to 1.0 parts, per part of tetrachloro-1,4-benzoquinone, or in a quantity of about 1%–10% by weight based on the reaction mixture.

13. The process as claimed in claim 1, wherein from 40% to 60% of the hydroquinone is introduced in step b).

14. The process as claimed in claim 1, wherein from 45% to 55% of the hydroquinone is introduced in step b).

15. The process as claimed in claim 1, wherein aqueous hydrochloric acid of a strength of about 31% is introduced in step a).

16. The process as claimed in claim 1, wherein the gaseous chlorine is introduced at a temperature of from 50° to 80° C. in step c).

17. The process as claimed in claim 1, wherein the residual quantity of hydroquinone added in step d) is added in the form of a from 15%–18% strength aqueous solution.

18. The process as claimed in claim 1, wherein the chlorination is carried out over 8.5 to 10.5 hours.

19. The process as claimed in claim 1, wherein the solvent is xylene, toluene, or diisopropylnaphthalene.

* * * * *